United States Patent [19]
Robinson

[11] Patent Number: 5,291,401
[45] Date of Patent: Mar. 1, 1994

[54] TELERADIOLOGY SYSTEM

[75] Inventor: Bruce T. Robinson, Telford, Pa.

[73] Assignee: Telescan, Limited, Berwyn, Pa.

[21] Appl. No.: 792,785

[22] Filed: Nov. 15, 1991

[51] Int. Cl.$^5$ .............................................. G06F 15/00
[52] U.S. Cl. ............................ 364/413.13; 364/413.14
[58] Field of Search ...................... 364/413.13, 413.14, 364/413.22

[56] References Cited

U.S. PATENT DOCUMENTS

| 4,748,511 | 5/1988 | Nichols et al. | 358/256 |
| 4,910,609 | 3/1990 | Nicholas et al. | 358/433 |

FOREIGN PATENT DOCUMENTS 0293083 11/1988 European Pat. Off. .

*Primary Examiner*—Roy N. Envall, Jr.
*Assistant Examiner*—Ari M. Bai
*Attorney, Agent, or Firm*—Mark A. Garzia; Eugene E. Renz, Jr.

[57] ABSTRACT

A teleradiology system for sending the raw data from a complete patient study to a remote location for a radiologist to make a final diagnosis. The system consists of two segments, a sending segment and a receiving segment. The sending segment consists of a universal floppy disk reading unit capable of reading raw data from a radiological device, (e.g., CAT Scanner, Nuclear Medicine Imaging device, Magnetic Resonance Imaging device, and the like) a personal computer, and a high speed modem. The receiving segment consists of a high speed modem to receive the data from the sending segment, a personal computer to control the receiving and manipulation of the data, and a high resolution monitor to view the images. The segments communicate through the modems and over existing telephone systems. At the remote location, the radiologist has the raw data and the capability of utilizing true windowing functions and true density values.

20 Claims, 3 Drawing Sheets

TELERADIOLOGY SYSTEM

BACKGROUND OF THE INVENTION

1. Field of the Invention

The present invention relates generally to a system for data acquisition and transmission. More particularly, the present invention relates to transmitting radiological images from a base radiology site to a remote site.

Teleradiology involves the transmission of digitized radiological images to an off-site or receive location for medical diagnosis purposes. The most common transmission site is a hospital; the usual receive site is the doctor's home or office.

When a patient or trauma victim is brought into a hospital, the patient may undergo one or more radiological processes. Current radiological processes include CAT or CT Scan (Computerized Axial Tomography), Magnetic Resonance Imaging (MRI), Nuclear Medicine Imaging (NMI), Ultrasound and X-ray. Depending on schedules, work-load, emergencies, budget constraints, etc., a radiologist may not be available in the hospital at any given time to read the image(s). With teleradiology, a radiologist can expand the territory covered by reviewing transmitted images at a remote office or site. Most frequently, the images are transmitted over standard telephone lines. However, with the advent of cellular telephones, digital cellular radio, fiber optics, and satellite communications, transmission medium is no longer limited to standard telephone lines.

In practice, an imaging or radiological device scans the traumatized tissue. The raw digitized data is converted to a video signal and displayed on the associated monitor or display device. Most imaging or radiological devices utilize a means for storing the raw data. Further, most imaging devices compress the raw data before it is stored. The most common storage devices are disc drives (either 8 inch, 5.25 inch or 3.5 inch), tape drives or laser disc drives. The storage medium is for archival purposes.

A radiological cross-sectional scan of a particular area of a patient's body is called a "slice". The slices are typically five (5) millimeters apart. A collection of slices is called a study. Although it may contain any number of slices, a typical study usually contains from 20 to 40 slices.

A data matrix may be used to depict each slice. The most common data matrix consists of 256 by 256 available data points. However, the matrix size can vary. For example, the Elscint CT Scan, model no. 1800, allows the operator to choose from three different matrix sizes, namely 256×256; 340×340; and 512×512. Each point within the matrix may be given a density value. A density value represents the density of the material found at a specific point within a slice.

Most CT scanners employ the Houndsfield scale to assign a numeric value to each density value. The Houndsfield scale ranges from minus 1000 to 3095. Air is assigned the numerical value of minus 1000, water is assigned the value of zero, and bone is assigned density values from 200 and up.

When viewing a slice, the radiologist is not looking at the entire range of the Houndsfield scale. Before a slice is displayed, the radiologist designates a "window". The window is a narrowing filter. In some instances, the window blocks as much as 98% of the raw data. A tissue window would be defined to check for internal bleeding and a bone window would be defined to check for bone fractures.

For example, if soft tissue is of particular interest, the radiologist defines a window ranging from zero to 100. In this example, any density value below zero appears as black on the CRT screen and any density value above 100 appears white. Density values within the defined range appear as shades of gray.

Nuclear Medicine Imaging devices use an analogous system to count the radioactive particles. The method of injecting a radioactive dye into a patient and measuring the radioactive particles given off, as the radioactive material decays, is known to those skilled in the art. An NMI device "counts" or detects the number of radioactive particles emitted. The count starts at zero and continues upwards.

Displaying all of the information at once, i.e., viewing soft tissue windows simultaneously with bone windows, would be virtually useless since there would be too many shades of gray for the human eye to distinguish between.

2. Description of the Prior Art

The typical teleradiology system utilizes available hardware and software to transfer video data from an imaging or radiological device to a remote viewing device. All known prior art teleradiology systems capture the filtered analog video signal generated by the radiology equipment and convert it to digital data by using a video digitizer or frame grabber. The frame grabber is usually connected to the video output jack of the radiological device's monitor. The frame grabber digitizes the analog video signal and forwards the digitized data to the teleradiology transmit computer. The digitized data is then transmitted to the remote location using a modem and standard telephone equipment. At the receiving site, the digitized video data is received by a second modem and converted back to a video signal and displayed on the remote CRT for the radiologist.

When the radiology equipment produces a plain film, e.g., an X-ray negative, a slightly different procedure is required. The film is placed on a light box. A video camera is pointed at the light box and the video signal from the video camera is connected to the frame grabber. The digitized data is then sent to the base site teleradiology computer for transmission to the remote site. Again, prior art teleradiology systems transmit the digitized video signal to the remote location.

In the normal operation of a prior art teleradiology system, an operator or technician located at the base or transmit site, establishes a communication link with the remote site. The radiologist conveys to the technician the desired windows and slices for viewing. The technician reviews the patient study by viewing the radiology device's monitor. The technician, in accordance with the doctor's instructions, selects a window and a slice. The raw digital data associated with the slice is filtered through the selected window. As a result of this filtration, raw data is lost. The filtered data is then converted to an analog video signal and displayed on the radiological device's monitor or CRT screen. The operator views that slice on the screen and decides whether to transmit that particular image to the remote site. If the technician decides that the slice is to be transmitted, the frame grabber of the teleradiology system is instructed to digitize the displayed image. The frame grabber responds by taking a digitized "snap-shot" of the image shown on the radiological device's display screen. The digitized data is then stored within the teleradiology system's transmit computer. The operator then repeats this process for each desired slice until the study is complete. This is a time consuming process. Furthermore, raw data has been lost since it has been filtered, converted into an analog video signal and then reconverted into a digital signal.

After completing the collection of filtered data, the technician advises the doctor that the desired study is ready for transmission to the remote site. The doctor at the remote site prepares to receive the information. The computer modems connect to establish a link and the data is transferred. The doctor will review the filtered data on the remote screen and may be able to make a preliminary diagnosis at this point. If the radiologist requires additional information, usually the same study using a different window, the doctor contacts the technician with instructions to set the new window and transmit the study.

The prior art teleradiology devices do not allow the radiologist at the remote site to control the true filtering or the true windowing of the images. Only a portion of the information available at the time the initial window is selected at the hospital can be sent to the remote site. If the radiologist wants to view the study with a different window filtering, the radiologist must instruct a technician at the hospital to refilter the study. After the frame grabber digitizes the signal and stores it within the base computer, it is transmitted to the remote site.

The technician must instruct the sending unit to digitize each slice as it is displayed on the base radiological device's CRT. The process needlessly occupies the technician's valuable time. Further, it increases the time before the radiologist has access to the information needed to make a diagnosis. This delays the treatment of the patient.

After receiving the requested data, the radiologist views the images, makes a preliminary diagnosis and instructs the hospital about the prescribed treatment. Usually, the radiologist at the remote site cannot make a final diagnosis on existing teleradiology systems since the raw data is not transmitted. At a later time, usually the next day, the radiologist will go to the base site and will review the study again with all available data to make a final diagnosis.

Since prior teleradiology systems only use the video signal, valuable information is not transmitted to, or viewed by the radiologist at the remote site. In prior art teleradiology systems, the doctor at the remote location can usually do no more than to look for gross abnormalities, such as fractures.

SUMMARY OF THE INVENTION

A teleradiology system is provided which includes a means for reading the raw data from the radiological device's storage medium, a means for studying the raw data, a means for transmitting the study to a remote location, a means for a receiving the data, a means for viewing the data and a means for filtering and manipulating the entire study.

The present invention utilizes the radiological device's storage medium and transmits the complete test data file without any filtering. Generally, only one transmission is needed under the present invention. The present invention does not derive its data from the analog video signal displayed on the base site imaging device.

Since the complete raw data file is transmitted, the radiologist at the remote site has complete control of the data filtration, i.e., true windowing capability, without requiring the subsequent intervention of a technician at the transmitting site.

Since the present invention transmits the complete file of density values to the radiologist, the radiologist can move a cursor onto a point of the displayed slice and obtain an exact readout of the density value at that point without possible loss of information due to filtration or signal conversion. This ability is invaluable when different types of information appear similar on the screen, such as in the case of a bone and a tumor. Ancillary patient data, such as the name, date, bed position, etc., is also transmitted with the study. Since the present invention allows the radiologist to make a final diagnosis from the remote site, valuable time is saved and the patient receives treatment sooner.

Since the present invention does not require a frame grabber, a significant savings can be realized over prior teleradiology systems. The present invention also has the ability to save the studies at the receiving station or remote site for future viewing.

It is the object of the present invention to provide the diagnosing physician with the raw unfiltered test data.

It is a further object to provide the raw data in a more rapid manner.

Another object of the present invention is to provide a teleradiology device with improved image fidelity.

A further object of the present invention is to provide an improved teleradiology system at a lower cost than those presently on the market.

Still another object of the present invention is to provide true windowing functions and true density measurement capability.

Other objects and advantages of the present invention will be apparent from the reading of the following detailed description of the presently preferred embodiment.

DETAIL DESCRIPTION OF THE PREFERRED EMBODIMENT

Figure 1:
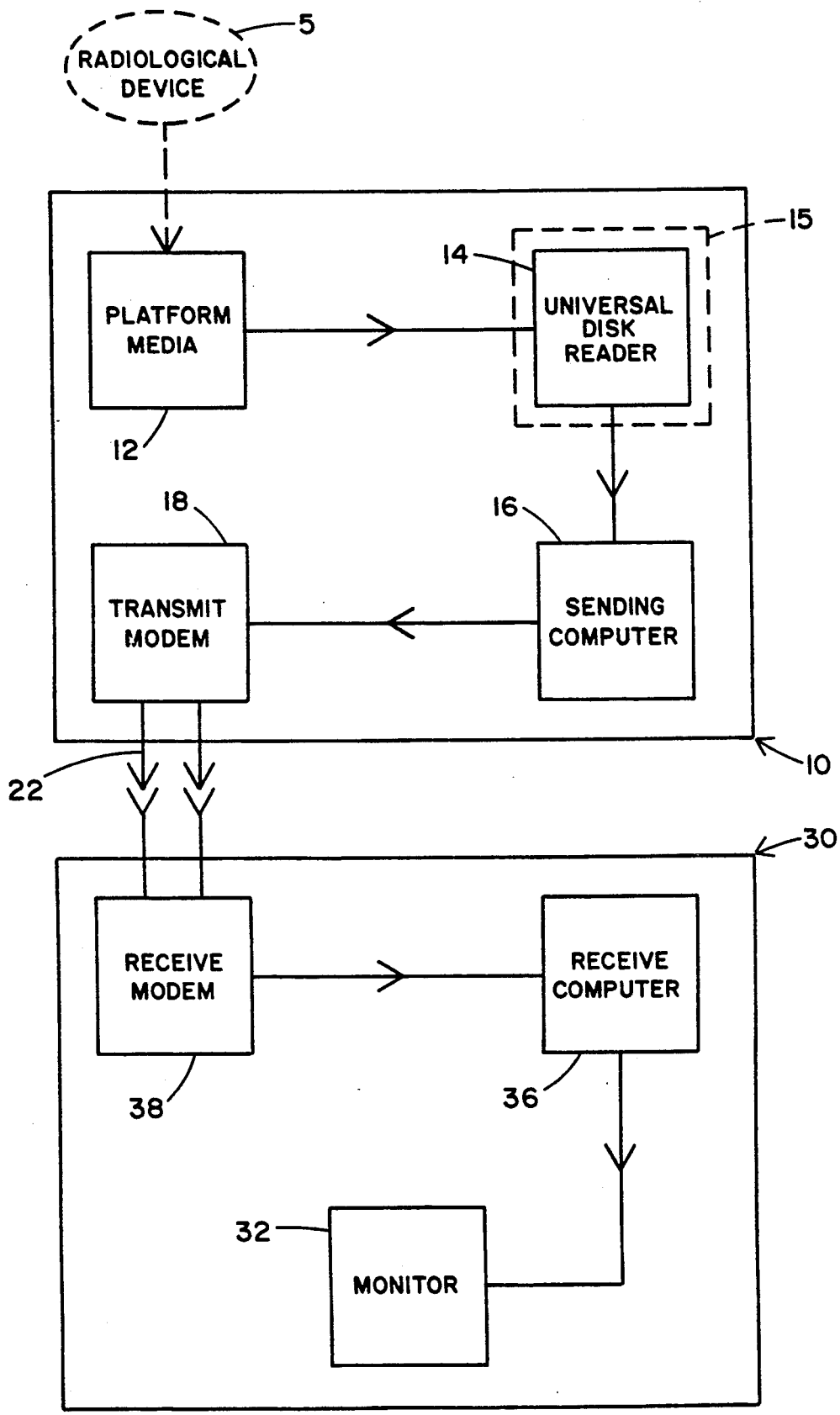
FIG. 1 is a block diagram of the teleradiology system in accordance with the present invention.

With reference to FIG. 1, the preferred embodiment is comprised of two segments or systems: a sending or transmitting unit and a receiving unit. The sending unit 10 is located proximate to the radiology equipment or device 5. The teleradiology sending unit 10 and radiological device 5 are usually located at a base site or hospital. The radiological device can be a CT Scanner, Magnetic Resonance Imaging device, Nuclear Medicine Imaging device, Ultrasound device, X-ray and the like. The receiving unit 30 is located at the remote site where the radiologist is located. Typically, this site is in the radiologist's home or office.

The sending unit 10 utilizes the same platform media 12 of the radiological equipment 5. The platform media 12 can be any type of electronic data storage medium. In the preferred embodiment, the platform media 12 may be a diskette (8 inch, 5.25 inch or 3.5 inch disk), tape drive or laser disk. The compressed raw digital data is stored on platform media 12 by the radiological device 5. The data from platform media 12 is input to the teleradiology system via a reading device 14. The preferred reading device 14 depends on the type of storage medium utilized by the radiological device and is most often a universal floppy disk reader or a nine-track tape reader. An example of the universal floppy disk reader is model no. FDD8532 manufactured by Flagstaff Engineering; an example of the nine-track tape is model no. 3201 manufactured by Overland Data.

A sending means 16 is connected to the reading device 14. The sending means 16 is typically an IBM PC or an IBM compatible computer with at least 640 k of memory. The preferred embodiment of the sending means 16 is a Zeos computer, model no. 386 SX-20. The operator at the base location can view the data from reading device 14 and store it in sending means 16, if so desired. Sending means 16 is preferably a computer system since this permits on-site review and since computers are commonly available.

A transmitting means 18, for example a high speed modem model Courier HST manufactured by U.S. Robotics, is connected to the computer 16 for transmitting the unfiltered raw data. Since compressed data is being transmitted, the transmission time is greatly reduced over prior teleradiology systems. The sending modem 18 transmits the unfiltered raw data to receiving means 38. The receiving means 38 may also be a high speed modem manufactured by U.S. Robotics, model Courier HST. The receive modem 38 is connected to a processing means or receive computer 36. The preferred embodiment employs an IBM PC or an IBM compatible, with 640 k of memory as the processing means 36. An example of an IBM compatible is Texas Instruments model Travelmate WIN-SX. After the study is transmitted, the transmission is terminated automatically. The receive computer 36 decodes the study and sounds an alarm to alert the radiologist that the study is now ready to be viewed.

Receive computer 36 decompresses the unfiltered raw data and can process it in the same manner as would be possible at the base site. A high resolution monitor 32 allows the radiologist to view the study at the remote site with all of the image fidelity as is available at the base site. In the preferred embodiment, the monitor 32 is available from Fast Micro as model Fast Data 14" white VGA monochrome monitor.

At this point, the radiologist has all of the information that would be available at the hospital or base site. Accordingly, a final diagnosis can be made at this point. The radiologist would then provide the instructions for the proper treatment and care of the patient to the personnel at the base site.

If it is desired to transmit data on plain film, e.g., X-ray negatives, a digital scanner 15, such as model no. Scan Jet II manufactured by Hewlett Packard may be used. In this instance a digital scanner is connected directly to the sending computer 16. This is shown in phantom in FIG. 1.

In either of the above examples, the radiologist can manipulate the data in virtually any manner desired without any further intervention by personnel at the base site. For example, the radiologist can view each consecutive slice in the appropriate order. Further, multiple slices can be viewed simultaneously. True windowing capability is available to the radiologist at the remote location. Reconstructions, where the radiologist can view the study from any cross-sectional angle, are also available.

The radiologist can place a cursor on the screen, move the cursor to a precise position on the slice and obtain the exact density value at that position.

With prior art teleradiology devices, the radiologist must be in constant communication with a technician at the hospital. The radiologist first relays instructions to the technician and the technician would then have to call up the desired image, store them, image by image, and then transmit them to the remote site.

With the preferred system the entire raw data file is sent in one transmission. The radiologist at the remote location can instantaneously access the complete study and has true windowing capability. Virtually all of the capabilities one has at the base site can be reproduced at the remote site.

Figure 2:
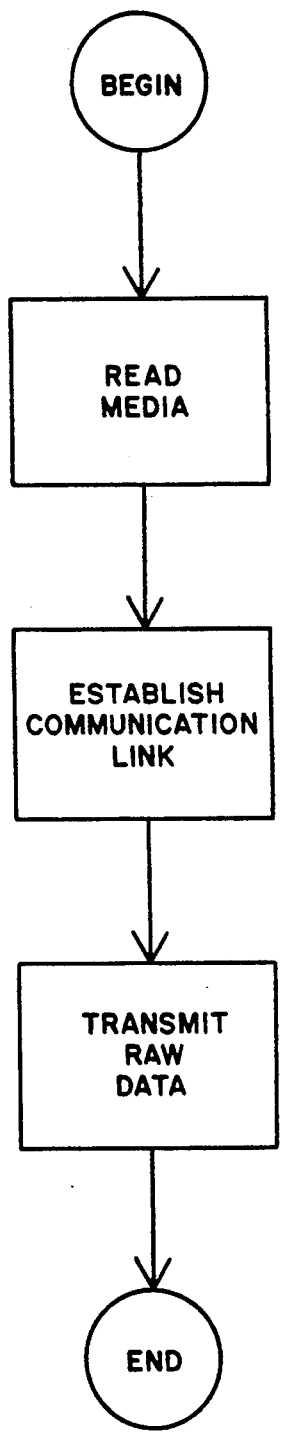
FIG. 2 is a flow diagram of the main functions performed by the transmission segment in accordance with the present invention.

With respect to FIG. 2, the raw data is read by the sending computer 16 off of the universal floppy disk reader 14 and stored internally. A communication link is established between the sending computer 16 and the receiving computer 36. The raw study data is then transmitted to the remote facility.

The radiological device usually compresses the data as a means of decreasing the number of diskettes needed to store the data. The present invention takes advantage of the data compression which allows all of the unfiltered, raw data produced by the radiological device to be transferred to the remote site in substantially the same transmission time as the prior art transmission. However, the present invention eliminates the technician time previously expended in preparing the data for transmission. In addition, physician time in instructing the technician in preparing the data is eliminated. Therefore, the physician has all of the data substantially simultaneously with the completion of the patient interrogation.

Figure 3:
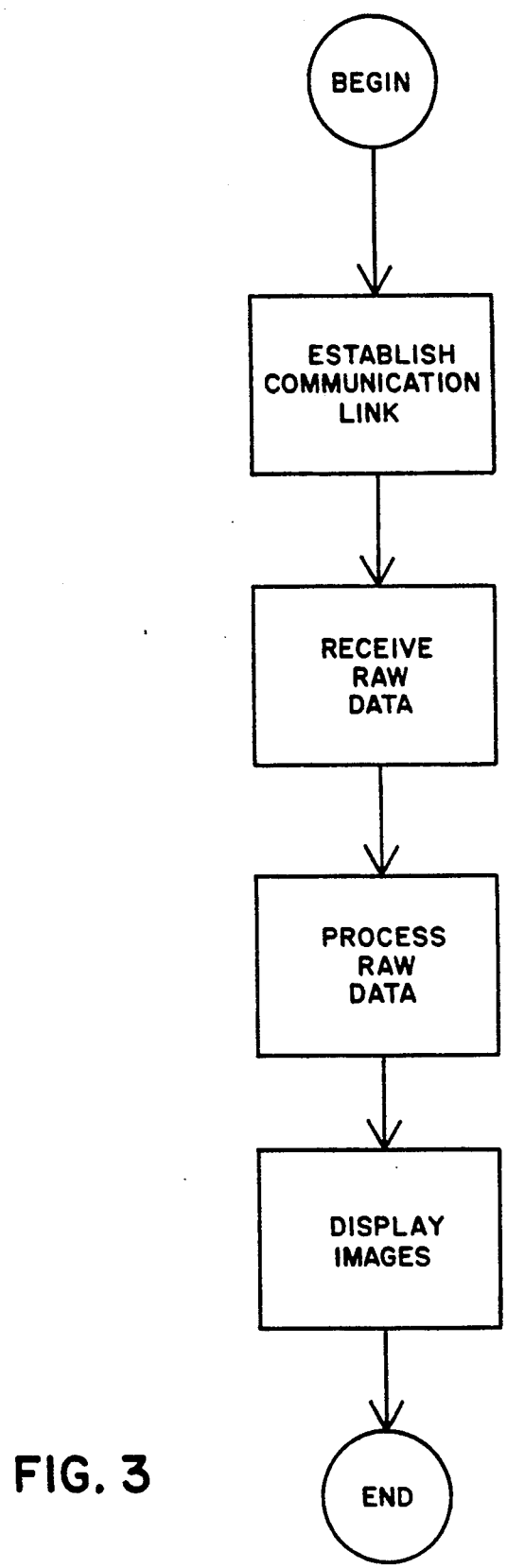
FIG. 3 is a flow diagram of the main functions performed by the receiver segment in accordance with the present invention.

With respect to FIG. 3, the receiving unit 30 first establishes a communication link with the sending unit 10. The raw data is transferred from the sending unit to the receiving unit and stored in received computer 36. The receive computer 36 decompresses the raw data and makes it available at the remote site in a format comparable to the original radiological device's format. The radiologist at the receive site can select a particular window and a particular study to view. The radiologist can manipulate the study through the use of the receive computer 36 and control the true window values.

With the preferred device, the radiologist can view eight different slices simultaneously. At this level of viewing, only 16 shades of gray are provided in the display. In order to provide a screen compatible with that at the base site, a high fidelity mode is also provided. This mode allows the radiologist to view a selected image or portion of an image on the full video screen with maximum gray scaling and image quality. Typically, the gray scaling at the base site is 64 shades of gray. Thus the present invention provides base site fidelity and the ability to view multiple slices simultaneously. Various windowing techniques can be employed to assist the radiologist in making the diagnosis.

Further, the ability to preserve ancillary data from the radiological device, such as the patient name, bed position, and the like, can be displayed.

In the preferred embodiment, the modem interface was developed using DataStorm Technology's Procom Plus programming language running under the Microsoft DOS operating system. The sending and receiving unit software was developed using Microsoft Quick Basic language (version 4.5) also running under the Microsoft DOS operating system.

What is claimed is:

1. A teleradiology system comprising:
   means for collecting raw digital data from a radiological device at a first location;
   means for transmitting the raw digital data, as collected, to a second location;
   means for receiving the transmitted digital data at the second location;
   means for processing the received digital data; and
   means for converting the processed digital data into analog signal to view at least one display image.

2. The system of claim 1 wherein the collecting means is a personal computer.

3. The system of claim 1 wherein the transmitting means is a high speed modem.

4. The system of claim 3 wherein the collecting means is a personal computer.

5. The system of claim 1 wherein the receiving means is a high speed modem.

6. The system of claim 5 wherein the transmitting means is also on high speed modem.

7. The system of claim 6 wherein the collecting means is a personal computer.

8. The system of claim 1 wherein the processing means is a personal computer.

9. The system of claim 8 wherein the collecting means is a personal computer.

10. The system of claim 9 wherein the transmitting means is a high speed modem.

11. The system of claim 10 wherein the receiving means is a high speed modem.

12. The system of claim 11 wherein the converting means is a high resolution monitor.

13. The teleradiology system of claim 1 wherein the converting means is a high resolution monitor.

14. The system of claim 13 wherein the collecting means is a personal computer.

15. The system of claim 13 wherein the transmitting means is a high speed modem.

16. The system of claim 13 wherein the receiving means is a high speed modem.

17. The system of claim 13 wherein the processing means is a personal computer.

18. A teleradiology diagnostic system comprising:
    a radiological device for interrogating a patient at a first location;
    means for collecting raw digital data from the radiological device at the first location;
    means for transmitting the raw data, as collected, to a second location;
    means for receiving the transmitted digital data at the second location;
    means for processing the received digital data; and
    means for converting the processed digital data into analog signal to view at least one display image.

19. A teleradiology diagnostic system consisting essentially of:
    a radiological device for interrogating a patient at a first location;
    means for collecting raw digital data from the radiological device at the first location;
    means for transmitting the raw digital data, as collected, to a second location;
    means for receiving the transmitted digital data at the second location;
    means for processing the received digital data; and
    means for converting the processed digital data into analog signal to view at least one display image.

20. A teleradiological method which comprises the steps of:
    collecting raw digital data from a radiological device at a base site;
    transmitting the raw digital data to a remote site;
    receiving the raw digital data at the remote site;
    processing the received digital data; and
    converting the processed digital data into analog signal to view at least one display image.

* * * * *